United States Patent [19]

Ramirez et al.

[11] Patent Number: 4,931,204

[45] Date of Patent: Jun. 5, 1990

[54] SELF-FOAMING OIL COMPOSITIONS AND PROCESS FOR MAKING AND USING SAME

[75] Inventors: Jose E. Ramirez, Trumbull; Mohan Vishnupad, Monroe, both of Conn.

[73] Assignee: Imaginative Research Associates, Inc., Bridgeport, Conn.

[21] Appl. No.: 270,263

[22] Filed: Nov. 14, 1988

[51] Int. Cl.$^5$ .................. C11D 3/18; C11D 3/43; C11D 3/44; C11D 3/48

[52] U.S. Cl. .................... 252/167; 252/49.5; 252/162; 252/163; 252/164; 252/165; 252/166; 252/168; 252/169; 252/170; 252/171; 252/549; 252/DIG. 5; 252/DIG. 13

[58] Field of Search ............... 252/DIG. 5, 167, 168, 252/162, 163, 164, 49.5, DIG. 13, 549, 170, 171, 169, 165, 166

[56] References Cited

U.S. PATENT DOCUMENTS

| | | | |
|---|---|---|---|
| 2,176,423 | 10/1939 | Jaegar | 260/481 |
| 2,995,521 | 8/1961 | Estignard-Bluard | 252/90 |
| 3,541,581 | 11/1970 | Monson | 252/90 |
| 3,941,722 | 3/1976 | Shevlin | 252/524 |
| 4,048,123 | 9/1977 | Hramchenko et al. | 252/545 |
| 4,405,489 | 9/1983 | Sisbarro | 252/315.4 |
| 4,554,098 | 11/1985 | Klisch et al. | 252/547 |
| 4,606,913 | 8/1986 | Aronson et al. | 424/59 |
| 4,626,529 | 12/1986 | Grollier | 514/159 |
| 4,652,389 | 3/1987 | Moll | 252/90 |
| 4,654,213 | 3/1987 | Ramirez et al. | 424/145 |
| 4,780,100 | 10/1988 | Moll | 8/137 |

Primary Examiner—Paul Lieberman
Assistant Examiner—A. Beadles-Hay
Attorney, Agent, or Firm—Perman & Green

[57] ABSTRACT

The present invention relates to liquid, lotion-like aqueous oil-in-water dispersion compositions including emulsions containing large amounts of oil or oil/wax mixtures, a volatile organic foam-producing liquid and an anionic surface active agent or detergent which increases the solubility of the foam-producing liquid in the oil or oil/wax mixture. The present compositions are dispersions including mixtures which do not foam or self-dispense from a non-pressurized container, and can be poured onto a surface and spread to form a thin coating which will foam and dry under ambient conditions to leave a residue of the oil or oil/wax mixture for cosmetic, medicinal, aesthetic, protective or other purposes.

18 Claims, No Drawings

SELF-FOAMING OIL COMPOSITIONS AND PROCESS FOR MAKING AND USING SAME

BACKGROUND OF THE INVENTION

Liquid compositions containing oils and/or soluble waxes are well known for a variety of uses, such as cosmetic lotions, medicinal lotions, furniture polishes, cleansers for tile, glass, metal, etc. Some such compositions contain soaps and/or detergents to enable them to entrap air and produce a foam or lather during use. However if high levels of oil or oil/wax mixture are added to such aqueous compositions, the foam- or lather-producing properties of the compositions are substantially reduced. Therefore aqueous liquid compositions, capable of being poured from a non-pressurized container to form a foam-producing coating, have not been available with oil or oil/wax contents greater than about 4% or 5% by weight. Such low contents are not satisfactory where the purpose of the product is to apply coatings which are high in oil or oil/wax content.

Aerosol compositions containing oil and/or oil/wax ingredients and water are also well known but such compositions must be dispensed as a foam from a pressurized container and cannot be contained as a self-foaming lotion-like liquid in a non-pressurized container. Reference is made to U.S. Pat. Nos. 2,655,480 and 3,705,855 for their disclosure of such aerosol compositions.

It is also known to provide aerosol soap and detergent compositions which dispense as a single phase gel capable of being spread over the skin as a self-foaming coating, and reference is made to U.S. Pat. Nos. 3,541,581, 4,505,489 and 4,772,427 for their disclosure of such compositions.

Finally, it is known from U.S. Pat. No. 4,726,944 to provide self-foaming or post foaming aqueous liquid detergent compositions which are capable of being poured from a non-pressurized container and rubbed into the hair as a post-foaming shampoo. Such compositions contain mixtures of anionic, amphoteric and non-ionic surfactants, water-soluble gum and a volatile hydrocarbon, and foaming occurs by evaporation of the latter as the composition is applied to the hair. U.S. Pat. No. 4,744,979 relates to similar post-foaming shaving gel compositions containing an aqueous soap solution and a mixture of surface active agents comprising amine oxides and alkanolamides.

While self-foaming or post-foaming compositions of the aforementioned types, capable of being poured as clear liquid solutions from a non-pressurized container, function well for their intended purposes, it has not been possible heretofore to produce lotion-like post-foaming compositions of these types which are detergent-based and contain large amounts of oil or oil/wax mixture for purposes of applying oil or oil/wax coatings to the skin or other surfaces for cosmetic, medicinal, aesthetic, protective, household, automotive or other purposes.

SUMMARY OF THE INVENTION

The present invention relates to the discovery of formulations for aqueous, lotion-like compositions which contain large amounts of dispersed oil or oil/wax mixture, greater than about 10% by weight, a volatile organic foam-producing liquid and an anionic surfactant or detergent which increases the solubility of the foam-producing liquid in the oil or oil/wax mixture which comprises the discontinuous phase of the composition, the continuous phase comprising water. This allows the presence of large amounts of the oil or oil/wax mixture without any interference with the foam-forming ability of the foam-producing liquid, whereby the composition can be poured onto a surface and spread as a creamy lotion coating which forms a uniform fine foam within a few seconds under ambient exposure, due to the evaporation of the volatile organic foam-producing liquid, to leave an oil or oil/wax foam residue which can be rubbed over the skin or other surface for cosmetic, medicinal, aesthetic, protective or other purposes. The presence of the oil or oil/wax on the skin during the foaming action permits the oil or oil/wax mixture, and any medicaments, emollients or other additives dissolved therein or present in the water phase to penetrate the skin and displace moisture, moisture-soluble dirt, skin oils or infected matter which may be withdrawn from the skin during the foaming process, for increased effectiveness in softening and treating the skin. These results cannot be obtained with aerosol foam compositions, which foam at the dispenser nozzle, or with prior-known post-foaming compositions which cannot contain significant amounts of oils or oil/wax mixtures and which do contain soaps and/or surfactants and/or other ingredients which prevent post-foaming in the presence of large amounts of oil or oil/wax mixtures and/or which are harsh on the skin or on other surfaces.

The preferred compositions of the present invention are aqueous emulsions including pseudo emulsions and other aqueous dispersions which can be agitated within the container, prior to use, to form lotion-like liquids containing oil or oil/wax mixture dispersed within the continuous water phase.

DETAILED DESCRIPTION

The present compositions contain at least about 10% by weight of one or more oils, alone or in combination with one or more waxes soluble in or compatible with said oil(s), at least about 5% by weight of at least one suitable anionic surface active agent or detergent, at least about 5% by weight of at least one volatile organic foam-producing liquid, and the remainder, generally less than about 60%, water.

The most critical ingredient of the present compositions from the standpoint of enabling the presence of large amounts of oil or oil/wax mixtures, is the anionic surface active agent or detergent. This material preferably is present in an amount within the range of from about 5% to about 20% by weight to enable the incorporation of from about 10% to about 60% by weight of the oil or oil/wax mixture. Cationic, non-ionic and amphoteric surface active agents or detergents are not satisfactory since they do not produce copious self-foaming or post-foaming compositions in the presence of amounts of oils or oil/wax mixtures greater than about 5% by weight.

Even among the anionic surface active agents or detergents, some materials such as sodium lauryl sulfate (referred to herein as SLS) and ammonium laurylether sulfate (referred to herein as ALS) do not increase the solubility of the volatile organic liquid in the oil or oil/wax mixture. Therefore the volatile liquid vaporizes to foam the composition within the container, prior to use, so that the composition self-dispenses from the container and is not functional for its intended purpose.

The most preferred mild anionic surfactants are sodium methyl cocoyl taurate (sodium salts of N-methyl taurine-coconut oil amides, referred to herein as SMCT); disodium cocamido monoisopropanol amide sulfosuccinate (disodium salts of sulfo-2-cocamide-1-methyl ethyl esters of butanedioic acid, referred to herein as DCMS); sodium lauryl sulfoacetate (sodium salt of sulfo-1-dodecyl ester of acetic acid, referred to herein as SLSA); and dioctyl sodium sulfosuccinate (sodium salt of the diester of 2-ethylhexyl alcohol and sulfosuccinic acid, referred to herein as DSS), combinations of such anionic detergents with each other or with small amounts of other foam-boosting surfactants.

Suitable oils for use in the compositions of the present invention include all of the conventional water-insoluble liquid or semi-solid mineral, vegetable, synthetic and animal oils, including fatty acid esters, lanolin, etc. The particular oils selected for a particular composition will depend upon its desired function and/or its ability to dissolve additives such as fragrances, waxes, medicaments, etc.

Suitable waxes include semi-solid and solid vegetable, mineral, animal and synthetic waxes, present in amounts which are soluble in the oils present to form liquid oil/wax mixtures.

The preferred volatile organic foam-producing liquids are those having a vapor pressure from about 4 to 14 p.s.i.g. at temperatures between about 90°–100° F., most preferably hydrocarbons having 5 or 6 carbon atoms such as isopentane, pentane and hexane. The volatile organic liquid preferably is present in an amount between about 5% and 15% by weight.

The final essential ingredient of the present compositions is water, which is present as an oil-in-water emulsion or dispersion to form the continuous phase of the self-foaming composition. Generally the water is present in an amount between about 25% and 60% by weight of the composition, most preferably between about 30% and 50% by weight.

Other ingredients generally are present in minor amounts, less than 10% by weight and usually less than about 2% by weight. Such additives should be soluble in or miscible with either the oils or oil/wax mixtures, or in the water, and include perfumes or fragrances, emollients, humectants, medicaments, colorants, etc.

The following examples are illustrative of several compositions within the scope of the present invention and should not be considered limitative. The compositions thereof are produced by adding the oils or oil/wax mixtures to a suitable container, adding the surface active agents or detergents thereto and homogenizing at a suitable elevated temperature until the detergents are thoroughly dispersed in the oil or oil/wax phase, water being added while homogenizing. Finally the mixture is cooled to room temperature or lower and the volatile organic foam-producing liquid, cooled to 5° C., is added while the composition is stirred with a mixer. Generally any additives are initially incorporated with the oils or oil/wax mixtures in the first step.

| Ingredients | Wt % |
|---|---|
| Example 1 | |
| Mineral Oil | 35.0 |
| DCMS | 15.0 |
| Water | 40.0 |
| Pentane | 10.0 |
| Example 2 | |
| Mineral Oil | 35.0 |
| DCMS | 13.0 |
| Sodium Lauryl Sulfate | 2.0 |
| Fragrance | 0.5 |
| Water | 39.5 |
| Isopentane | 10.0 |
| Example 3 | |
| Mineral Oil | 35.0 |
| SMCT | 15.0 |
| Water | 40.0 |
| Pentane | 10.0 |
| Example 4 | |
| Mineral Oil | 35.0 |
| DCMS | 20.0 |
| Water | 35.0 |
| Pentane | 10.0 |
| Example 5 | |
| Mineral Oil | 35.0 |
| DCMS | 5.0 |
| Water | 50.0 |
| Pentane | 10.0 |
| Example 6 | |
| Petroleum Jelly | 15.0 |
| Mineral Oil | 10.0 |
| Isopropyl Palmitate | 10.0 |
| DCMS | 12.0 |
| SLS | 3.0 |
| Water | 39.5 |
| Fragrance | 0.5 |
| Isopentane | 10.0 |
| Example 7 | |
| Mineral Oil | 35.0 |
| SLSA | 5.0 |
| Water | 50.0 |
| Isopentane | 10.0 |
| Example 8 (Shaving Preparation) | |
| Mineral Oil | 15 |
| Isopropyl Palmitate | 10 |
| Glycerine | 10 |
| DCMS | 13 |
| SLS | 2 |
| Water | 40 |
| Isopentane | 10 |
| NaOH to adjust to pH10 | |
| Example 9 (Antidandruff cleanser) | |
| Mineral Oil | 35.0 |
| DCMS | 15.0 |
| Omadine MDS (MgSO$_4$ adduct) | 1.0 |
| Water | 39.0 |
| Isopentane | 10.0 |
| Example 10 (Psoriatic Skin Cleanser) | |
| Petroleum Jelly | 10.0 |
| Mineral Oil | 20.0 |
| DCMS | 15.0 |
| Coal Tar Aqueous Soln. | 5.0 |
| Water | 40.0 |
| Isopentane | 10.0 |
| Example 11 (Auto Cleaner/Polish) | |
| Carnauba Wax | 17.5 |
| Mineral Oil | 17.5 |
| DCMS | 9.0 |
| SLS | 1.0 |
| Water | 45.0 |
| Isopentane | 10.0 |
| Example 12 (Cosmetic Cleanser) | |
| Mink Oil | 35.0 |
| DCMS | 15.0 |
| Water | 40.0 |
| Isopentane | 10.0 |
| Example 13 (Cosmetic Cleanser) | |
| Lanolin | 10.0 |
| Acetulan (acetylated lanolin) | 25.0 |
| DCMS | 13.0 |
| SLS | 2.0 |
| Water | 40.0 |
| Isopentane | 10.0 |
| Example 14 | |
| DCMS | 15.0 |

| Ingredients | Wt % |
|---|---|
| Mineral Oil | 60.0 |
| Water | 15.0 |
| Isopentane | 10.0 |
| *Example 15* | |
| DCMS | 5.0 |
| Mineral Oil | 35.0 |
| Water | 50.0 |
| Isopentane | 10.0 |
| *Example 16* | |
| SCT | 15.0 |
| Mineral Oil | 10.0 |
| Water | 65.0 |
| Isopentane | 10.0 |
| *Example 17* | |
| DSS | 15.0 |
| Mineral Oil | 35.0 |
| Water | 40.0 |
| Isopentane | 10.0 |
| *Example 18* | |
| DCMS | 12.0 |
| SLS | 3.0 |
| Mineral Oil | 20.0 |
| Petroleum Jelly | 12.5 |
| Polyethyleneglycol-8 Dilaurate | 2.5 |
| Water | 39.5 |
| Fragrance | 0.5 |
| Hexane | 10.0 |
| *Example 19 (Depilatory Lotion)* | |
| DCMS | 15.0 |
| Mineral Oil | 35.0 |
| Water | 34.0 |
| Calcium Thioglycolate | 6.0 |
| Isopentane | 10.0 |

In order to establish the critical nature of the anionic surface active agent or detergent in the present compositions, the compositions of Example 1, 3, 7 and 17 were compared with compositions identical thereto except for the substitution of identical amounts of the following surface active agents for the surface active agents of the Examples:

(a) SLS (anionic)
(b) ALS (Anionic)
(c) Nonoxinol 9 (non-ionic)
(d) Dimethyl-1-naphthyl methyl ammonium chloride (cationic)
(e) Cocamphocarboxyl glycinate (amphoteric)

Each of the compositions, Examples 1, 3, 7, 17, a, b, c, d and e, was placed in an individual 100 ml graduated cylinder, 10 ml of water was added to 10 gms. of each composition, and the cylinder was closed and shaken vigorously ten times. The initial and final volumes of the foam were recorded as 1 (0 ml increase), 3 (27 ml increase), 7 (0 ml increase), 17 (0 ml increase), a (55 ml increase), b ( 59 ml % increase), c (8 ml increase), d (5 ml decrease) and e (28 ml increase). The preferred compositions, Examples 1, 7 and 17, showed no tendency to foam in the sealed container under agitation, establishing the solubilizing effect of the volatile organic liquid and its suppression against escape and foaming within the container, whereby the compositions have excellent post-foaming properties after being poured onto the skin and wiped into a thin coating. The composition of Example 3 foamed 50% less than compositions a and b and still solubilized the volatile organic liquid within the oil to a sufficient extent that the composition has excellent post-foaming properties similar to those of Examples 1, 7 and 17. The compositions of a and b foamed excessively and self-dispensed from the container, although they do post-foam because the volatile liquid is solubilized in the oil phase but only to an unsatisfactory low extent.

Conversely, compositions c, d and e, while they showed little or no tendency to foam when agitated in the sealed container, they were non-functional when poured onto the skin and spread in the same manner as the other compositions since they do not self-foam or post-foam to any useful extent.

Therefore it will be apparent to those skilled in the art that the various classes of oils or oil/wax mixtures, specific ones of which are illustrated by the various examples set forth herein, can be incorporated in large amounts in self-foaming compositions capable of being contained within non-aerosol, non-pressurized containers, preferably small-mouth rigid containers, which compositions can be poured onto the skin or other surface and rubbed or spread in the same manner as a conventional lotion and will self-generate a copious foam on the skin or other surface in a few seconds time. The foaming operation results from the evaporation of the organic foam-producing liquid to leave an oily foam residue which can be rubbed into the skin or over a wooden, metallic, plastic or other surface for cleaning, medication, polishing, waxing or other purposes.

It is to be understood that the above described embodiments of the invention are illustrative only and that modifications throughout may occur to those skilled in the art. Accordingly, this invention is not to be regarded as limited to the embodiments disclosed herein but is to be limited as defined by the appended claims.

What is claimed is:

1. Aqueous, lotion-like, flowable liquid oil-in-water dispersion or emulsion composition, containing large amounts of oil or oil/wax mixture, which is capable of being contained within a non-pressurized container without self-foaming and capable of being poured onto a surface and spread as a thin layer to self-develop a copious foam, said compositions comprising an aqueous emulsion or dispersion having a continuous aqueous phase and a discontinuous phase comprising at least about 10% by weight based upon the total weight of the composition, of at least one oil or oil/wax mixture, at least about 5% by weight based upon the total composition, of a volatile organic foam-producing liquid which has an evaporation temperature at or slightly above ambient room temperature, and at least about 5% by weight based upon the total weight of the composition, of at least one anionic surface active agent selected from the group consisting of sodium methyl cocoyl taurate, disodium cocamido mono isopropanolamide sulfosuccinate, sodium lauryl sulfoacetate and dioctyl sodium sulfoccinate which increases the solubility of said foam-producing liquid in the oil or oil/wax mixture of said discontinuous phase, and water comprising said continuous aqueous phase.

2. A composition according to claim 1 comprising from about 10% to 60% by weight of said oil oil/wax mixture, from about 5% to 20% by weight of said anionic surface active agent, from about 5% to 15% by weight of said volatile organic liquid and from about 30% to 60% by weight of water.

3. A composition according to claim 1 in which said volatile organic liquid is one having a vapor pressure from about 4 to 14 p.s.i.g. at a temperature between 90° and 100° F.

4. A composition according to claim 3 in which said volatile organic liquid comprises pentane, isopentane or hexane.

5. A composition according to claim 1 in which said oil comprises mineral oil or a mineral oil/petroleum jelly mixture.

6. A composition according to claim 1 containing a mixture of two different anionic surface active agents.

7. A composition according to claim 1 further containing minor amounts of one or more oil-soluble or water-soluble additives for imparting fragrance, emollient, cosmetic, medication, humectant or other properties to said composition.

8. A shaving composition according to claim 7 in which said oil comprises a fatty acid ester and said additives include a humectant and sufficient alkali to render said composition alkaline.

9. An anti-dandruff shampoo composition according to claim 7 in which said additives include an anti-dandruff agent.

10. A psoriatic composition according to claim 7 in which said additives include an aqueous coal tar solution.

11. Process for producing an aqueous, lotion-like, flowable liquid oil-in-water dispersion or emulsion composition, having a continuous aqueous phase and a discontinuous phase comprising large amounts of oil or oil/wax mixture, which is capable of being contained within a non-pressurized container without self-foaming and capable of being poured onto a surface and spread as a thin layer to self-develop a copious foam, which comprises mixing together a composition comprising at least about 10% by weight based upon the total weight of the composition of at least one oil or oil/wax mixture, at least about 5% by weight based upon the total weight of the composition of a volatile organic liquid which has an evaporation temperature at or above room temperature, at least about 5% by weight based upon the total weight of composition of at least one anionic surface active agent selected from the group consisting of sodium methyl cocoyl taurate, disodium cocamido mono isopropanolamide sulfosuccinate, sodium lauryl sulfoacetate and dioctyl sodium sulfosuccinate which increases the solubility of said volatile organic liquid in said oil or oil/wax mixture, and water, and homogenizing said mixture to form an oil-in-water dispersion having a continuous aqueous phase and a discontinuous phase comprising said foam-producing liquid dissolved within the dispersed oil or oil/wax phase.

12. A process according to claim 11 which comprises mixing from about 10% to 60% by weight of said oil or oil/wax mixture, from about 5% to 20% by weight of said anionic surface active agent, from about 5% to 15% by weight of said volatile organic liquid and from about 30% to 60% by weight of water.

13. A process according to claim 11 in which said volatile organic liquid is one having a vapor pressure from about 4 to 14 p.s.i.g. at a temperature between 90° and 100° F.

14. A process according to claim 13 in which said volatile organic liquid comprises pentane, isopentane or hexane.

15. A process according to claim 11 in which said oil comprises mineral oil or a mineral oil/mineral wax mixture.

16. A process according to claim 11 in which said mixture contains two different anionic surface active agents.

17. A process according to claim 11 in which said mixture further contains minor amounts of one or more oil-soluble or water-soluble additives for imparting fragrance, emollients, cosmetic, medication, humectant or other properties to said composition.

18. A process for applying a thin coating of oil or oil/wax composition to a surface for cosmetic, aesthetic, protective, medication, cleansing or other purposes, which comprises producing a self-foaming lotion-like, flowable liquid aqueous oil-in-water dispersion comprising a continuous aqueous phase and a discontinuous phase comprising at least about 10% by weight based upon the total weight of the composition of oil or oil/wax mixture, at least about 5% based upon the total weight of the composition of a volatile organic foam-producing liquid, and at least about 5% based upon the total weight of the composition of at least one anionic surface active agent selected from the group consisting of sodium methyl cocoyl taurate, disodium cocamido mono isopropanolamide sulfosuccinate, sodium lauryl sulfoacetate and dioctyl sodium sulfosucinate which increases the solubility of the foam-producing liquid in the oil or oil/wax so that said liquid remains dissolved to a substantial extent within the oil or oil/wax until the composition is spread as a thin layer on a surface exposed to the atmosphere, pouring said lotion-like flowable liquid dispersion onto a surface to be treated and spreading it as a thin layer exposed to ambient conditions, whereby said composition self-develops a copious foam due to the evaporation of said volatile foam-producing liquid, which foam contains said oil or oil/wax mixture and can be rubbed into or over said surface to provide a cosmetic, aesthetic, protective, medication, cleansing or other coating thereon.

* * * * *